United States Patent
Arifin et al.

(10) Patent No.: US 9,995,725 B2
(45) Date of Patent: Jun. 12, 2018

(54) PHASE FRACTION MEASUREMENT USING LIGHT SOURCE ADJUSTED IN DISCRETE STEPS

(71) Applicant: SCHLUMBERGER TECHNOLOGY CORPORATION, Sugar Land, TX (US)

(72) Inventors: Arifin Arifin, Singapore (SG); Cheng-Gang Xie, Singapore (SG)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days. days.

(21) Appl. No.: 15/194,853

(22) Filed: Jun. 28, 2016

(65) Prior Publication Data
US 2017/0370896 A1 Dec. 28, 2017

(51) Int. Cl.
G01N 33/28 (2006.01)
G01N 21/31 (2006.01)
G01F 1/74 (2006.01)

(52) U.S. Cl.
CPC .......... *G01N 33/2823* (2013.01); *G01F 1/74* (2013.01); *G01N 21/314* (2013.01)

(58) Field of Classification Search
CPC ..... G01N 33/2823; G01N 21/314; G01F 1/74
USPC .......................................................... 356/70
See application file for complete search history.

(56) References Cited

U.S. PATENT DOCUMENTS

| 3,841,144 A | 10/1974 | Baldwin |
| 4,131,815 A | 12/1978 | Boatright |
| 4,240,287 A | 12/1980 | Mast et al. |
| 5,167,149 A | 12/1992 | Mullins et al. |

(Continued)

FOREIGN PATENT DOCUMENTS

| EP | 1192457 B1 | 1/2013 |
| WO | WO2005088415 A1 | 9/2005 |
| WO | 2010133875 A1 | 11/2010 |

OTHER PUBLICATIONS

Nabipour et al.—SPE158580—Methods for Measurement of Solid Particles in Hydrocarbon Flow Streams, SPE Asia acific Oil and Gas Conference and Exhibition held in Perth, Australia, Oct. 22-24, 2012 (14 pages).

(Continued)

*Primary Examiner* — Hina F Ayub
(74) *Attorney, Agent, or Firm* — Cameron R. Sneddon

(57) ABSTRACT

Disclosed herein is an apparatus including a structure containing a multiphase fluid and having a transparent window. A collimated light source emits light through the transparent window structure at a wavelength at which a component of a desired phase of the multiphase fluid is absorptive. A photodetector is positioned such that the emitted light passes through the multiphase fluid in the structure and out through the transparent window structure to impinge upon the photodetector. The photodetector has an actual dynamic range for light detection. Processing circuitry adjusts a power of the collimated light source in a series of steps dependent upon a relationship between an output level of the photodetector and a threshold to cause measurement of the emitted light over an effective dynamic range greater than the actual dynamic range. Properties of the multiphase fluid are determined as a function of the measured emitted light.

20 Claims, 7 Drawing Sheets

(56) References Cited

U.S. PATENT DOCUMENTS

| | | | |
|---|---|---|---|
| 6,118,520 | A | 9/2000 | Harner |
| 7,233,001 | B2 | 6/2007 | Lievois et al. |
| 7,503,217 | B2 | 3/2009 | Johansen |
| 7,578,203 | B2 | 8/2009 | Andersen et al. |
| 7,834,312 | B2 | 11/2010 | Lievois et al. |
| 8,285,491 | B2 | 10/2012 | Xie et al. |
| 8,615,370 | B2 | 12/2013 | Ong |
| 9,234,420 | B2 | 1/2016 | Xie |
| 2008/0231860 | A1 | 9/2008 | Melnyk |
| 2010/0007896 | A1* | 1/2010 | Fishbaine .......... G01N 21/8806 356/603 |
| 2012/0112072 | A1 | 5/2012 | Jones et al. |
| 2013/0009048 | A1 | 1/2013 | Xie et al. |
| 2013/0016336 | A1 | 1/2013 | Xie |
| 2013/0328402 | A1 | 12/2013 | Noguchi |
| 2015/0101419 | A1* | 4/2015 | Hill .......................... G01F 1/74 73/861.04 |
| 2015/0338547 | A1 | 11/2015 | Moise et al. |
| 2016/0170136 | A1* | 6/2016 | Johansen ........... G02B 6/02333 356/479 |

OTHER PUBLICATIONS

International Search report and written opinion issued in the related PCT application PCT/US2017/038642, dated Sep. 29, 2017 (11 pages).

Office Action Issued in the related U.S. Appl. No. 15/194,829, dated Jan. 13, 2017 (18 pages).

Notice of Allowance Issued in the related U.S. Appl. No. 15/194,829, dated Aug. 23, 2017 (10 pages).

\* cited by examiner

PHASE FRACTION MEASUREMENT USING LIGHT SOURCE ADJUSTED IN DISCRETE STEPS

BACKGROUND

This invention is related to the field of phase fraction measurement of a multiphase fluid, and, more particularly, to a multiphase flowmeter for making such phase fraction measurements.

DESCRIPTION OF THE RELATED ART

In hydrocarbon production, fluid produced from wells and flowing through various points of a production system is multiphasic. Thus, the fluid may have any of a gas phase, an oil phase, a water phase, and a solid phase. For a variety of reasons, it can be desirable to know the fraction of the fluid represented by each phase. For example, the presence of solids, such as sand, in fluid can result in the erosion of equipment of a production system and even damage.

Multiphase flowmeters may be used to determine these phase fractions. A multiphase flowmeter may be installed in tubing and may employ a radioactive source and scintillation detector to enable measurement of the phase fractions. Such multiphase flowmeters have proven to be accurate and desirable.

Due to challenging regulatory environments, however, the fact that a multiphase flowmeter utilizes a radioactive source may be undesirable. In addition, current multiphase flowmeters may be prohibitively expensive for use in wells with relatively low rates of production.

Therefore, a commercial desire exists for further development in the area of multiphase flowmeters.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Disclosed herein is an apparatus including a pipe through which a multiphase fluid flows with a transparent window structure formed in the pipe. A collimated light source is configured to emit light through the transparent window structure and into the pipe with the emitted light having a wavelength at which a component of a desired phase of the multiphase fluid is absorptive. A photodetector is positioned such that the emitted light passes through the multiphase fluid in the pipe and out through the transparent window structure to impinge upon the photodetector. The photodetector has an actual dynamic range for collimated light detection. Processing circuitry coupled to the collimated light source and photodetector is configured to continuously adjust a power of the collimated light source dependent upon an output level of the photodetector so as to cause measurement of the emitted light by the photodetector over an effective dynamic range greater than the actual dynamic range. The processing circuitry also determines at least one property of the multiphase fluid as a function of the power of the collimated light source.

A method aspect is directed to a method of determining at least one property of a multiphase fluid. The method includes emitting collimated light into the multiphase fluid, with the emitted light having a wavelength at which a component of a desired phase of the multiphase fluid is absorptive. Light passing through the multiphase fluid that impinges upon a photodetector having an actual dynamic range for collimated light detection is detected. A power of the collimated light source is continuously adjusted dependent upon an output level of the photodetector so as to cause measurement of the emitted light by the photodetector over an effective dynamic range greater than the actual dynamic range. At least one property of the multiphase fluid is determined as a function of the power of the collimated light source.

Another aspect is directed an apparatus including a structure containing a multiphase fluid, with a transparent window structure formed in the structure. A collimated light source is configured to emit light through the transparent window structure and into the structure, with the emitted light having a wavelength at which a component of a desired phase of the multiphase fluid is absorptive. A photodetector is positioned such that the emitted light passes through the multiphase fluid in the structure and out through the transparent window structure to impinge upon the photodetector. The photodetector has an actual dynamic range for collimated light detection. Processing circuitry is coupled to the collimated light source and photodetector. The processing circuitry is configured to adjust a power of the collimated light source in a series of steps dependent upon a relationship between an output level of the photodetector and at least one threshold so as to cause measurement of the emitted light by the photodetector over an effective dynamic range greater than the actual dynamic range. The processing circuitry is also configured to determine at least one property of the multiphase fluid as a function of the measured emitted light.

Another method aspect is directed to a method of determining at least one property of a multiphase fluid. The method includes emitting collimated light into the multiphase fluid, with the emitted light having a wavelength at which a component of a desired phase of the multiphase fluid is absorptive. Light passing through the multiphase fluid and impinging upon a photodetector having an actual dynamic range for collimated light detection is detected. A power of the collimated light source is adjusted in a series of steps dependent upon a relationship between an output level of the photodetector and at least one threshold so as to cause measurement of the emitted light by the photodetector over an effective dynamic range greater than the actual dynamic range. At least one property of the multiphase fluid is determined as a function of the measured emitted light.

Still another aspect is directed to an apparatus that includes a pipe through which a multiphase fluid flows, with a transparent window structure formed in the pipe. A collimated light source is configured to emit light through the transparent window structure and into the pipe, where the emitted light has a wavelength at which a component of a desired phase of the multiphase fluid is absorptive. A photodetector is positioned such that the emitted light passes through the multiphase fluid in the pipe and out through the transparent window structure to impinge upon the photodetector. The photodetector has an actual dynamic range for collimated light detection. Processing circuitry is coupled to the collimated light source and photodetector and configured to adjust a power of the collimated light source so as to cause measurement of the emitted light by the photodetector over an effective dynamic range greater than the actual dynamic range. The processing circuitry is also configured to determine at least one property of the multiphase fluid as a function of the measured emitted light and/or the power of the collimated light source Various refinements of the features noted above may exist in relation to various aspects of the present embodiments. Further features may also be incorporated in these various aspects as well. These refinements and additional features may exist individually or in any combination. For instance, various features discussed below in relation to the illustrated embodiments may be incorporated into any of the above-described aspects of the present disclosure alone or in any combination. Again, the brief summary presented above is intended just to familiarize the reader with certain aspects and contexts of some embodiments without limitation to the claimed subject matter.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

It is to be understood that the present disclosure provides many different embodiments, or examples, for implementing different features of various embodiments. Specific examples of components and arrangements are described below for purposes of explanation and to simplify the present disclosure. These are, of course, merely examples and are not intended to be limiting.

When introducing elements of various embodiments, the articles "a," "an," "the," and "said" are intended to mean that there are one or more of the elements. The terms "comprising," "including," and "having" are intended to be inclusive and mean that there may be additional elements other than the listed elements. Moreover, any use of "top," "bottom," "above," "below," other directional terms, and variations of these terms is made for convenience, but does not mandate any particular orientation of the components.

Figure 1:
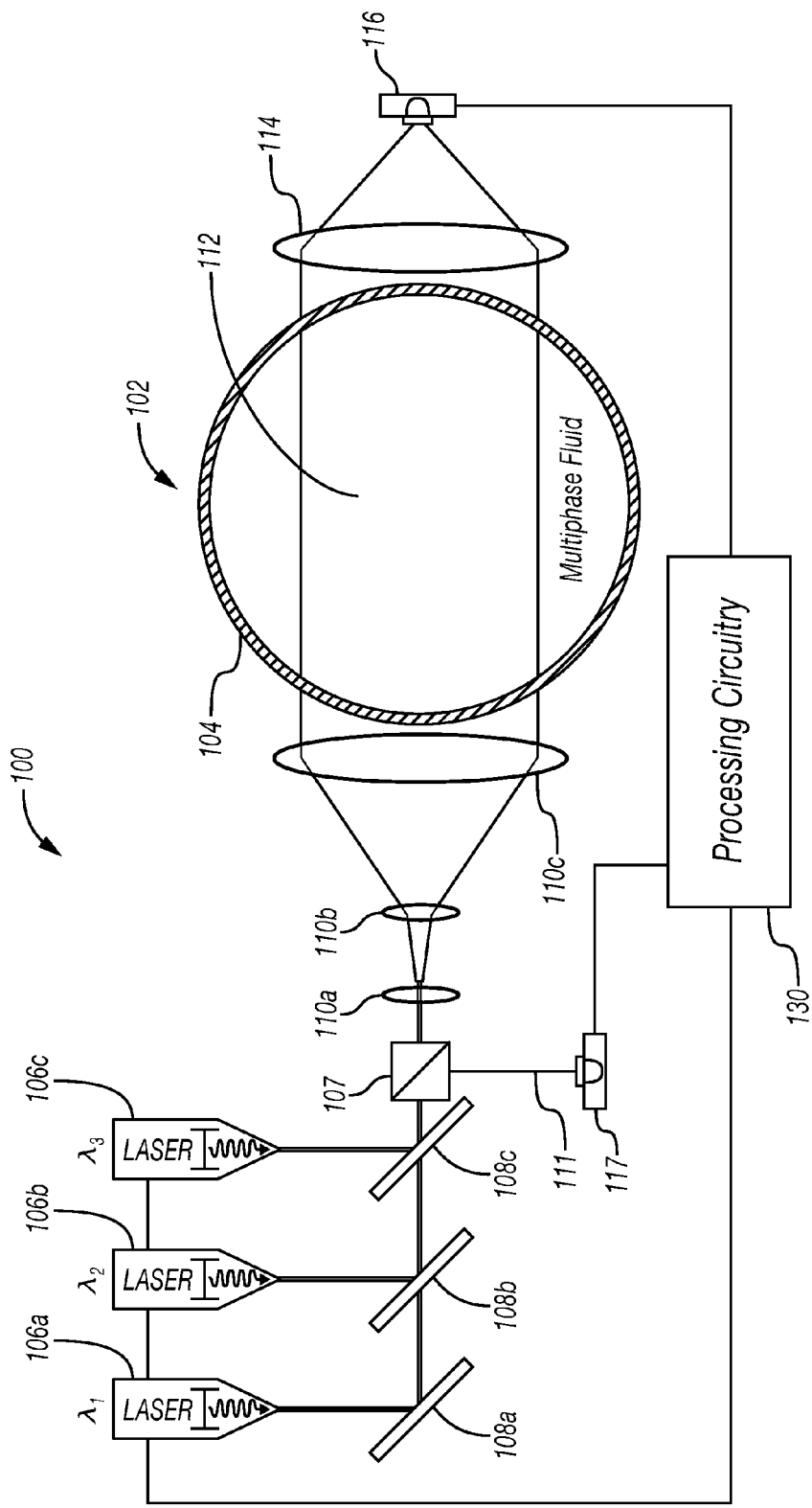
FIG. 1 is a schematic block diagram of a phase fraction determination system capable of discriminating among three phases, in accordance with this disclosure.

Referring initially to FIG. 1, a phase fraction determination system 100 is now described. The system includes a pipe or tube 102 through which a multiphase fluid flows. The multiphase fluid may have any of three or four phases, which include a gas phase, oil phase, a water phase, and solid phase. The gas phase and oil phase are hydrocarbon bearing. "Gas" is used here to denote any form of hydrocarbon bearing gas, and "oil" is used generically here to denote any form of hydrocarbon oil.

As shown, the cross section of the pipe 102 is circular, although in some applications, a pipe 102 with a rectangular or square cross section may be used. The pipe 102 may have a relatively small radius, for example on the order of 5 mm-30 mm; where the pipe 102 has a rectangular cross section, the dimensions may be on the order of 10 mm-30 mm×2 mm-6 mm, for example, or even larger. Where the pipe 102 has a rectangular cross section, the cross sectional area can be increased for the same path length as in a pipe 102 with a circular cross section. Other suitable radiuses and dimensions may be used in appropriate applications as well as other structures in addition to pipe 102.

A window 104 is formed in the pipe 102. The window 104 is illustratively cylindrical in shape, although other shapes may be used. The window 104 may be formed from synthetic sapphire. Where the pipe 102 is rectangular in cross section, the window 104 may be rectangular in cross section, or may be two separate windows located on opposite sides of the pipe 102. The window 104 is optically transparent to the wavelengths of collimated light emitted by the collimated light sources, such as, for example, lasers 106a-106c, as will now be explained.

The collimated light sources or lasers 106a-106c are illustratively laser light sources employing laser diodes and emitting laser light in the near-infrared wavelength spectrum, although other types of laser light sources may be employed in some applications. Each laser 106a-106c emits light in a different narrow wavelength spectrum. For example, laser 106a emits light having a wavelength of $\lambda 1$, corresponding to a wavelength where oil is substantially more absorptive than water.

Dichroic mirrors 108a-108c respectively combine the collimated light from the lasers 106a-106c on an optical path through the window 104 and into the multiphase fluid. It should be noted that where the cross section of the pipe 102 is rectangular, the mirrors 108a-108c are configured to direct the collimated light from the lasers 106a-106c across the shorter path length available in the rectangular cross section, and not the longer path.

The lasers 106a-106c need not be perfectly aligned along the optical path, and would function effectively if they were not aligned along the optical path but converged on and focused on the same spot of the photodetector 116. Thus, in some applications, mirrors that are not dichroic may be used.

In some applications, rather than dichroic mirrors 108a-108c, other devices may be used to reflect and combine the collimated light from the lasers 106a-106c. Such other device may be polarized beam splitters or unpolarized beam splitters, for example.

In the optical path from the lasers 106a-106c, a beam splitter 107 may be used to split the power of the lasers. A small power-fraction beam 111 measured by a photodetector 117 (with a thermally-stable optical attenuator if useful) may monitor the variations in laser output over time and compensate for power changes due to temperature variations and device aging. The majority of the power from the lasers 106a-106c passes through the beam splitter 107, and is delivered to the window 104 through a series of cylindrical lenses 110a-110c that serve to shape the emitted light into a nearly two dimensional ribbon 112 shape, for example having dimensions of 15 mm×0.5 mm, that passes through substantially all, or a substantial majority of, or an entire cross section of, the cross section of the pipe 102. A lens 114, on the far side of the pipe 102, focuses the two dimensional light ribbon 112 as it exits the pipe 102 for detection by a photodetector 116. From the spectrum of light impinging on the photodetector 116, or from the output power of the lasers 106a-106c monitored by the photodetector 117, phase fractions of the multiphase fluid can be determined by the processing circuitry 130, which receives output signals from the photodetectors. The photodetectors 116 and 117, as well as the collimated light sources 106a-106c, may be thermally stabilized by active cooling or heating to achieve stable measurements.

In order to enable the photodetectors 116 and 117 to separately and independently measure the intensities of the outputs from the lasers 106a-106c, the lasers 106a-106c are temporally multiplexed such that but one of the lasers 106a-106c is emitting light at once. Stated another way, the temporal multiplexing results in laser 106a emitting light while lasers 106b-106c are not, laser 106b emitting light while lasers 106a, 106c are not, and laser 106c emitting light while lasers 106a-106b are not. A limitation of this temporal multiplexing is that the flow rate of the multiphase fluid should be substantially less than the total time elapsed for each laser 106a-106c to activate once in turn. For example, where each laser 106a-106c is activated for 30 μs, the total interrogation time is thus 90 μs. Where the ribbon of collimated light 112 has a thickness of 0.5 mm, the instantaneous velocity of the multiphase fluid should remain less than 1.4 m/s.

Alternatively, instead of temporal multiplexing, the lasers 106a-106c may be operated simultaneously but at different pulsing frequencies. These frequencies are chosen so as to be reasonably far away from multiphase fluid fluctuation frequencies in order to enable the use of phase-sensitive detection (PSD) of the light impinging on the photodetectors 116 and 117 by the processing circuitry 130 to provide for discrimination between components of the light impinging on the photodetectors 116 and 117 that were emitted by the first laser 106a, components of the light impinging upon the photodetectors 116 and 117 that were emitted by the second laser 106b, and components of the light impinging upon the photodetectors 116 and 117 that were emitted by the third laser 106c. By using PSD, the processing circuitry 130 also functions to attenuate erroneous readings from the photodetectors 116 and 117 caused by stray light events.

The use of PSD may realize multi-wavelength measurements simultaneously and for multiphase flows at the same location in the pipe. Higher quality signals may be obtained by, as explained, rejecting stray lights automatically by PSD, and phase fractions may be measured more accurately due to the simultaneous data detection at multiple wavelengths.

As will be explained in detail below, the processing circuitry 130, in addition to determining the phase fractions of the multiphase fluid, acts to control the lasers 106a-106c as a function of the light detected by the photodetector 116.

Details of operation will now be given with reference to FIG. 5. A useful wavelength for $\lambda_1$ is a hydrocarbon peak absorption band at which hydrocarbons, such as oil and gas, are a few times to a few thousand times more absorptive of light than water. A useful wavelength for $\lambda_2$ is at a lower end of a water peak absorption band, at which water is substantially more absorptive of light than hydrocarbons, such as oil and gas. In addition, a useful wavelength for $\lambda_3$ is a band at which neither water nor oil is substantially absorptive.

Figure 5:
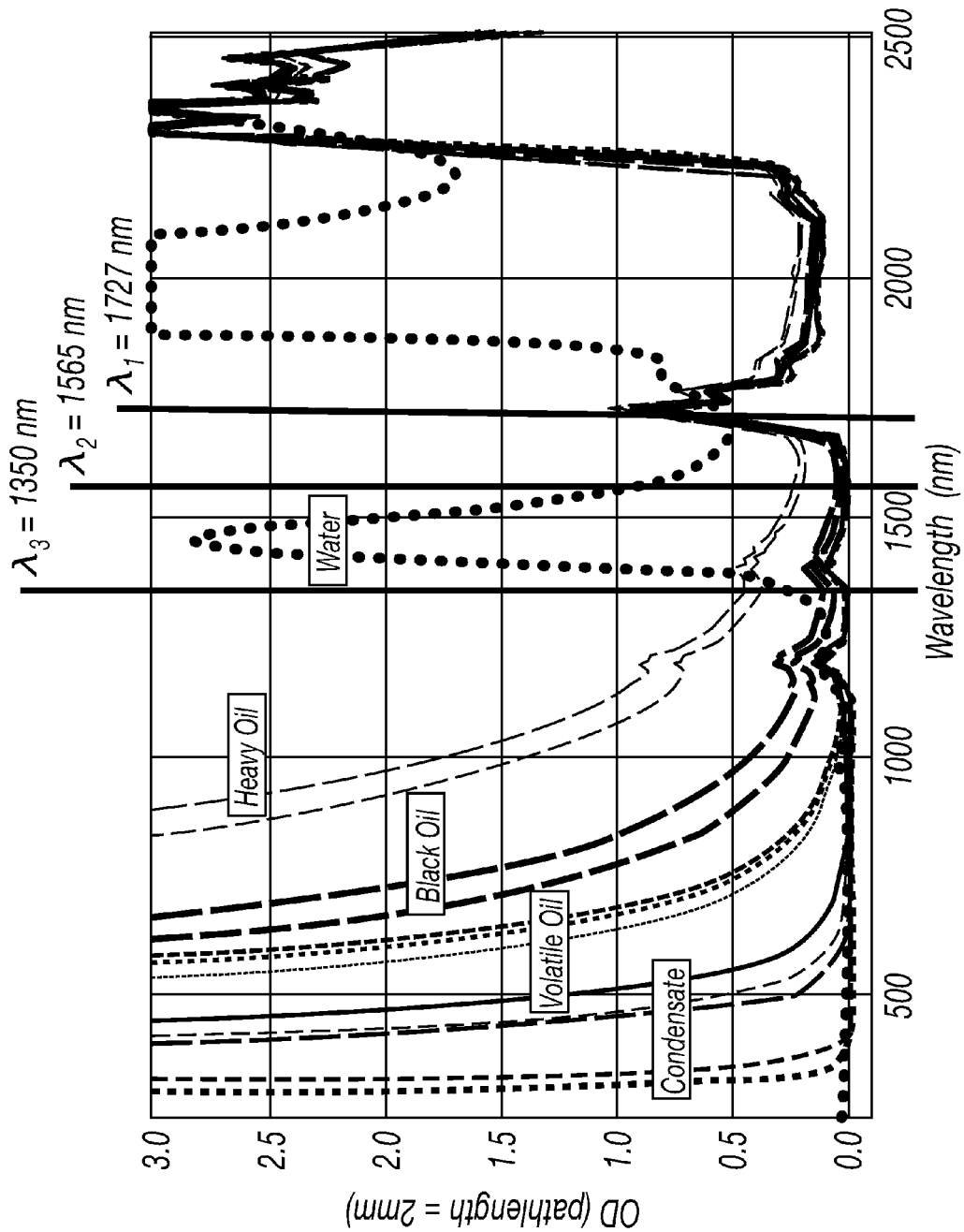
FIG. 5 is a graph showing transmission absorption optical density for various hydrocarbon oils and water.

As an example, as shown in FIG. 5, $\lambda_1$ may be at the hydrocarbon peak, which is between 1693 nm and 1757 nm, for example in some cases at 1727 nm, and at which hydrocarbons such as oil and gas are a few times to a few thousand times more absorptive of light than water. $\lambda_2$ may be at the lower end of the water peak or water absorption band, around 1565 nm, where water is substantially more absorptive of light than hydrocarbons such as oil and gas. $\lambda_3$ may be at 1350 nm, which is at a relatively low point on the absorption spectrum of interest, such that any attenuation or absorption can be understood to be due to bubbles, droplets, or solids, and at which components of the oil and water phases are not substantially absorptive. Thus, in some embodiments, the third collimated light source or laser 106c may have a third wavelength at which components of the first and second phases of the multiphase fluid are not absorptive.

Figure 7:
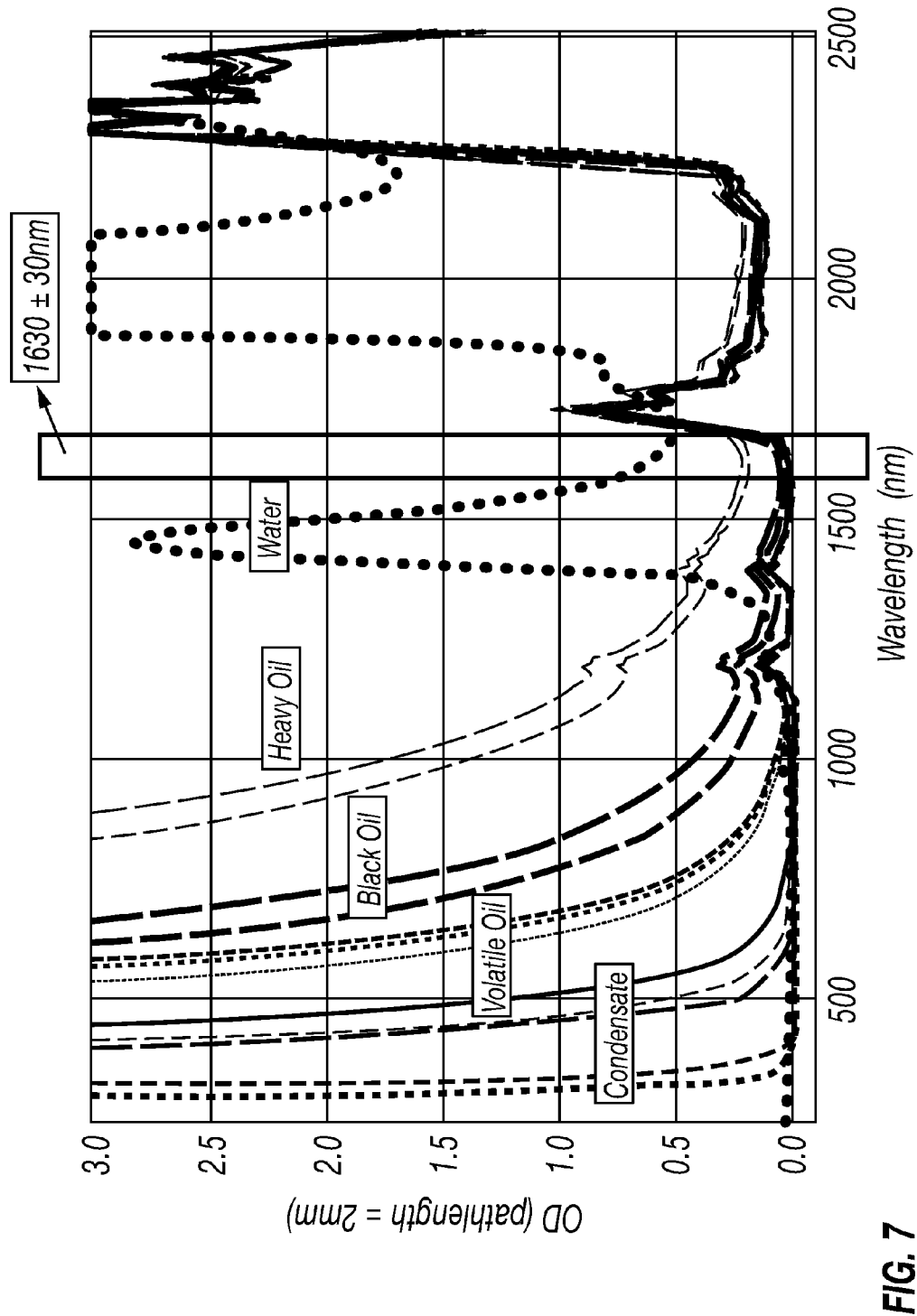
FIG. 7 is a further graph showing transmission absorption optical density for various hydrocarbon oils and water.

The wavelengths $\lambda_1$, $\Delta_2$, and $\lambda_3$ are such that the optical densities of the phases of the multiphase fluid do not exceed undesirable amounts which would render the emitted collimated light undetectable under attenuation. Shown in FIG. 5 is a graph of optical density (OD) verses wavelength including the above discussed wavelengths $\lambda_1$, $\lambda_2$, and $\lambda_3$. As can be seen from FIG. 5, the optical densities at the wavelengths $\lambda_1$, $\lambda_2$, and $\lambda_3$ do not exceed 0.5 per millimeter path length. Using a pipe 102 having a diameter of 19 mm, the optical density could reach 9.5, which correlates to an attenuation of 109.5 times. With a diode laser emitting light at a 350 mW output power, after attenuation, approximately 0.1 mW of output power could be detected, which is detectable by conventional InGaAs, InAsSb, or germanium photodetectors with an acceptable signal to noise ratio. A similar example may be found in FIG. 7. Here, the hydrocarbon peak is around 1630 nm.

Figure 6:
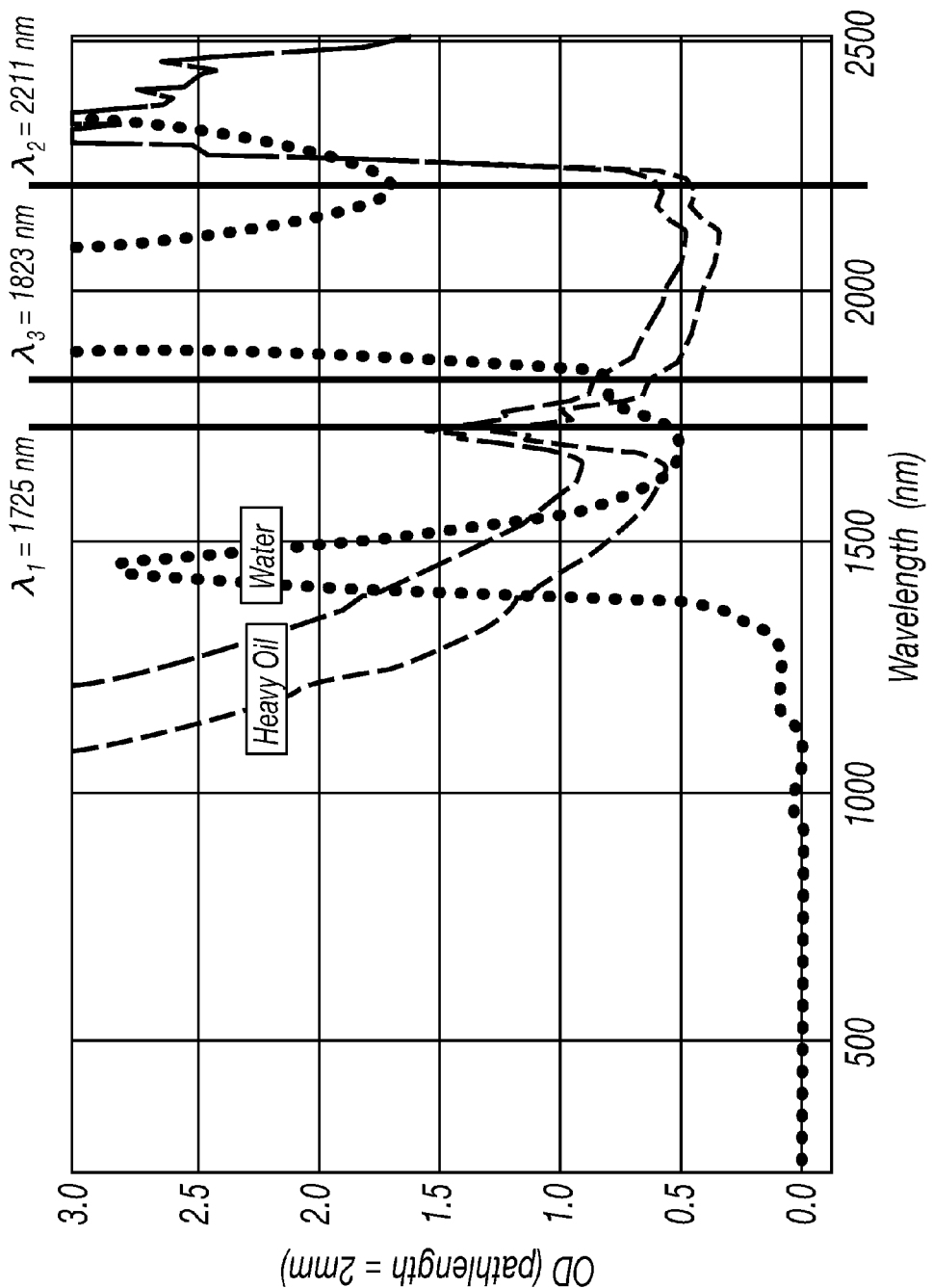
FIG. 6 is another graph showing transmission absorption optical density for various hydrocarbon oils and water.

For certain heavy oils, however, the optical density at the wavelengths $\lambda_1$, $\lambda_2$, and $\lambda_3$ is greater than those shown in FIG. 5. Therefore, in some instances, different and more appropriate values for $\lambda_1$, $\lambda_2$, and $\lambda_3$ may be used. Here, $\lambda_1$ may be selected as 1725 nm, $\lambda_2$ may be selected as 2211 nm, and $\lambda_3$ may be selected as 1823 nm, as shown in FIG. 6. However, the optical density at these wavelengths $\lambda_1$, $\lambda_2$, and $\lambda_3$ is on the order of 0.8 per millimeter, meaning that to obtain the same detection of 0.1 mW of output power, the diameter of the pipe 102 has to be reduced from 19 mm to 12 mm. An alternative to reduction of diameter of the pipe 102 is to use an avalanche photodiode or photomultiplier tube as the photodetector 116. It should be noted that where the cross section of the pipe 102 is rectangular, the collimated light at the wavelengths $\lambda_1$, $\lambda_2$, and $\lambda_3$ may be made to measure the optical density across the shorter path length (such as 5 mm) in the rectangular cross section, and not across the longer path length (such as 22 mm). The phase fraction determination system 100 may adjust the wavelengths of the lasers based on knowledge from oil samples.

As should be appreciated, the photodetector 116 (or the photodetector 117) has a dynamic range of light intensity that is capable of detecting up to 3 to 4 times the optical density range of state-of-the-art photodetectors. However, to determine phase fractions over a full gas volume fraction range, light intensities outside the actual dynamic range of the photodetector 116 are to be detected. Therefore, as will be described below, techniques may be employed in order to operate the photodetector 116 or 117 with an effective dynamic range that is greater than the actual dynamic range.

The actual dynamic range of the photodetector 116 or 117 is the difference between the lowest intensity of light that the photodetector 116 or 117 can detect and the highest intensity of light that the photodetector 116 or 117 can discriminate. Light having an intensity greater than the highest intensity of light that the photodetector 116 or 117 can discriminate, or light having an intensity less than the lowest intensity of light that the photodetector 116 or 117 can detect, is said to be outside of the actual dynamic range of the photodetector 116 or 117. Stated another way, the actual dynamic range of the photodetector 116 or 117 is the difference between the smallest and largest usable signal producible by the photodetector 116 or 117.

The effective dynamic range of the photodetector 116 or 117 can be made to be greater than the actual dynamic range using the techniques described herein. The above effective dynamic range extension is achieved by continuously adjusting the output power of the lasers 106a-106c in real time (which is monitored by the photodetector 117 with the use of known optical attenuation means if desired), as a function of the output level of the photodetector 116 such that the output level of the photodetector 116 remains constant. It should be appreciated that designs where there are an equal number of photodetectors 116 to the number of lasers 106a-106c are within the scope of this disclosure.

When operating as per this first technique, since the intensity/power level at the photodetector 116 is constant while the output power level of the lasers 106a-106c fluctuates (and is monitored by the photodetector 117), the processing circuitry 130 monitors the current consumption or power level of the lasers 106a-106c in order to determine the phase fractions of the multiphase fluid. Due to the continuous real time adjustment of the output power of the lasers 106a-106c, the photodetector 116 is prevented from saturating. Thus, independent of the attenuation provided by the various phases of the multiphase fluid, the lasers 106a-106c may at times have output powers outside of the actual dynamic range of the photodetector 116. Since the lasers 106a-106c are monitored to determine the phase fractions of the multiphase fluid and since the photodetector 116 is prevented from saturating, the output power of the lasers 106a-106c may at times exceed the actual dynamic range of the photodetector 116, yet measurements may still accurately be made. Due to this technique, the nonlinearity of the photodetector 116 may be irrelevant and have no effect on results.

A second technique for operating the photodetector 116 at an effective dynamic range greater than the actual dynamic range is where the processing circuitry 130 adjusts the output power of the lasers 106a-106c in a series of steps dependent upon a relationship between an output level of the photodetector and at least one threshold. In greater detail, the processing circuitry 130 switches the output power of the lasers 106a-106c from a higher level (or step) to a lower level (or step) in a discrete step when the output level of the photodetector 116 exceeds an upper threshold, and switches the output power of the lasers 106a-106c from a lower level (or step) to a higher level (or step) in a discrete step when the output level of the photodetector 116 falls below a lower threshold. Thus, the output level of the lasers 106a-106c remains constant between the higher threshold and lower threshold.

A specific example of this second technique is now described. For example, for a 19 mm diameter pipe 102, it is desirable for the photodetector 116 to be capable of detecting light intensities from 0.1 mW to 350 mW, which corresponds to nine orders of magnitude. Yet, the actual dynamic range of the photodetector 116 is merely five orders of magnitude. This desired effective dynamic range of nine orders of magnitude may thus be divided into three intensity stages, each of which covers three orders of magnitude. As the processing circuitry 130 detects the photodetector 116 nearing saturation (thus, the output of the photodetector 116 rises beyond an upper threshold), it discretely reduces the output power of the lasers 106a-106c to a lower level.

Similarly, when the processing circuitry 130 detects the output of the photodetector 116 falling below a lower threshold, it discretely increases the output power of the lasers 106a-106c to a higher level.

Here, the processing circuitry 130 analyzes the outputs of the photodetectors 116 and 117 in order to determine the phase fractions of the multiphase fluid. In addition, as with the first technique, since the photodetector 116 is prevented from saturating, the output power of the lasers 106a-106c may at times exceed the actual dynamic range of the photodetector 116, yet measurements may still accurately be made.

Processing of either the output $V_\lambda$ of the photodetector 116, which is a DC voltage proportional to the light intensity $I_\lambda$ detected by the photodetector 116, or output power $I_{o,\lambda}$ of the lasers 106a-106c measured by the photodetector 117, by the processing circuitry 130 is now described. For a given wavelength $\lambda$, the light intensity signal acquired from the photodetector 116 $I_\lambda$ or the lasers 106a-106c $I_{o,\lambda}$ is proportional to the intensity of the transmitted light ($I_\lambda$). Accounting for scattering due to bubbles/droplets, this can be mathematically represented using the Beer-Lambert law, and can be written as:

$$I_\lambda = I_{0,\lambda}[e^{-\Sigma_i \alpha_i \chi_{i,\lambda} d} K(\alpha_i, \zeta, \lambda, d)],$$

where $i \in \{\text{oil, water, gas}\}$, $\chi_i$ represents the linear attenuation coefficient of the phases obtained from a fluid-sample reference measurement, and $K(\alpha_i, \zeta, \lambda, d)$ represents a general scattering term which is dependent on the phase fractions $\alpha_i$, bubble/droplet size and geometrical factor $\zeta$, wavelength $\lambda$, and pipe diameter d. Excluding Rayleigh scattering (i.e. scattering by particles much smaller than the wavelength), the scattering term K would generally be independent of wavelength.

Using the signal from $\lambda_3$, the scattering term (K) can be factored out, and the set of equations reduces to the following:

$$\begin{bmatrix} \chi_{w,\lambda 1} & \chi_{w,\lambda 3} & \chi_{o,\lambda 1} & \chi_{o,\lambda 3} & \chi_{g,\lambda 1} & \chi_{g,\lambda 3} \\ \chi_{w,\lambda 2} & \chi_{w,\lambda 3} & \chi_{o,\lambda 2} & \chi_{o,\lambda 3} & \chi_{g,\lambda 2} & \chi_{g,\lambda 3} \\ & 1 & & 1 & & 1 \end{bmatrix} \cdot \begin{bmatrix} \alpha_w \\ \alpha_o \\ \alpha_g \end{bmatrix} = \begin{bmatrix} R(I_{\lambda 1}, I_{\lambda 3}) \\ R(I_{\lambda 2}, I_{\lambda 3}) \\ 1 \end{bmatrix}$$

where, $$R(I_{\lambda 1}, I_{\lambda 3}) = \frac{1}{d} \ln\left( \frac{I_{0,\lambda 1}}{I_{0,\lambda 3}} \frac{I_{\lambda 3}}{I_{\lambda 1}} \right)$$

$$R(I_{\lambda 2}, I_{\lambda 3}) = \frac{1}{d} \ln\left( \frac{I_{0,\lambda 2}}{I_{0,\lambda 3}} \frac{I_{\lambda 3}}{I_{\lambda 2}} \right)$$

The matrix on the left is called the relative attenuation matrix where the scattering effect has been subtracted. The values of the matrix elements can be obtained from full-bore or calibration-cell measurements on each phase (i.e. in-situ reference). Once the matrix is known, the phase fraction could be calculated upon inversion of this matrix. For robustness, this matrix is to be invertible and to have a determinant much larger than zero. Those of skill in the art will understand that the equations above are an example for the case where determination of the phase fraction for three phases is performed, but that these equations can be generalized to account for a fourth phase, such as sand. In fact, these equations can be generalized to account for any number of phases, such as a fifth phase that is hydrogen sulfide.

Figure 2:
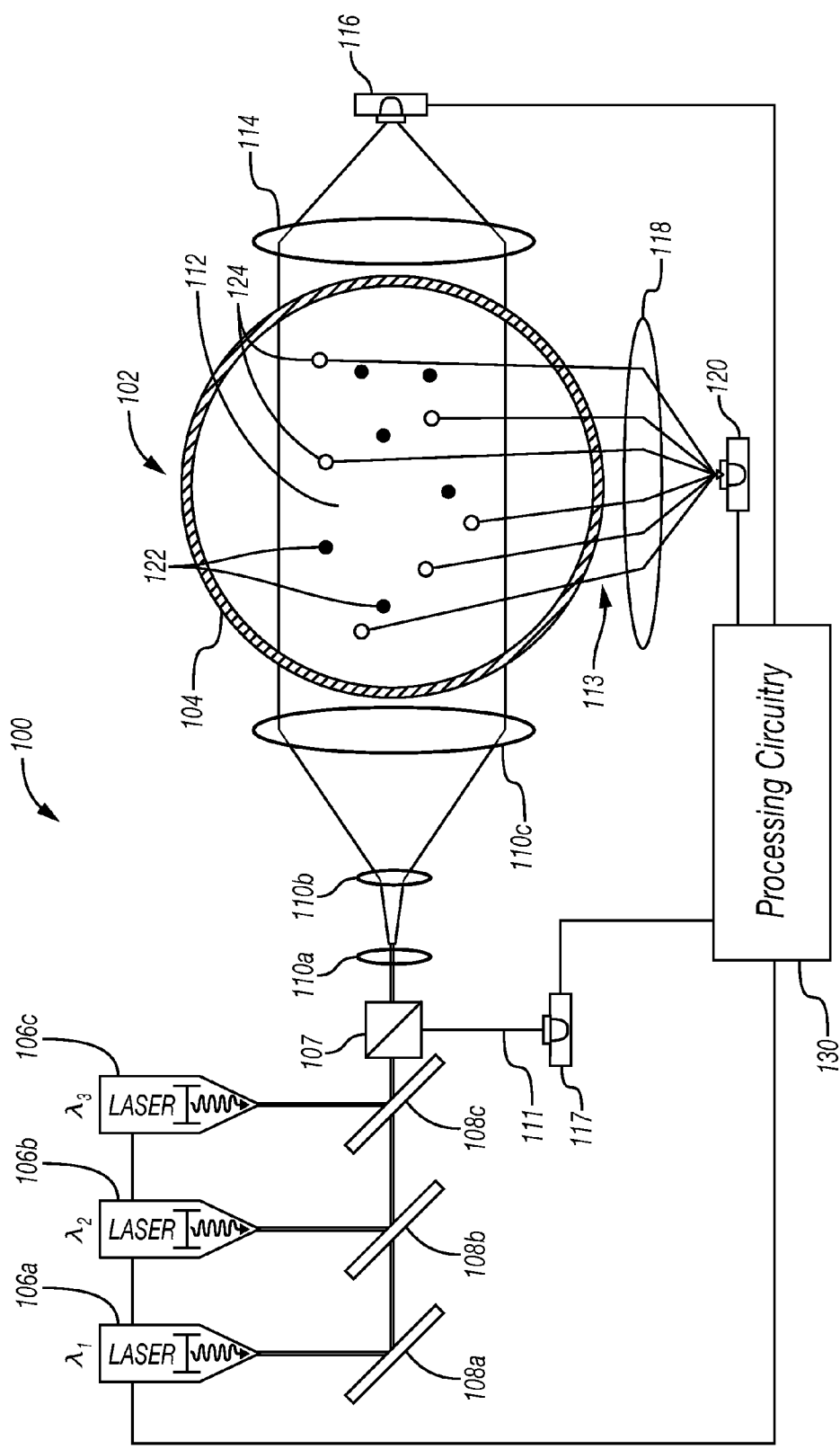
FIG. 2 is a schematic block diagram of a phase fraction determination system capable of discriminating among four phases, in accordance with this disclosure.

The system 100 described above is useful for determining the phase fractions of gas, oil, and water. However, in some instances, the multiphase fluid may include a solid phase (such as sand particles), and it may be desirable to know the phase fraction of the solid phase as well. To that end, the system 100 may be modified to measure the fourth (solid) phase as will now be described with reference to FIG. 2.

Added to the system 100 in this embodiment is a lens 118 perpendicular to the lenses 110a-100c and 114, that serves to focus light 113 reflected or scattered from solids 122 or sand in the multiphase fluid for detection by an additional photodetector 120. Through the function and calculations described above, together with data from the additional photodetector 120, the processing circuitry 130 may determine a phase fraction for the solid phase.

During operation, the output of the photodetector 116 (and thus the intensity of collimated light impinging on the photodetector 116) is monitored and measured over time by the processing circuitry 130. Since the intensity of collimated light impinging on the photodetector 116 fluctuates over time due to the phase composition of the multiphase fluid, and in particular due to the presence of solids 122 or sand grains, and bubbles or droplets 124, this measured intensity over time yields a pattern of intensity values, where some intensity values are greater than others.

By performing analysis on this pattern of intensity values and matching the pattern of intensity values to known patterns, the processing circuitry 130 can determine the presence of sand grains. For example, using a pattern correlation, fitting, or matching technique, such as chi-square or residual sum, the processing circuitry 130 may, in the time domain, compare the pattern of intensity values to a known intensity value pattern or set of patterns that indicate presence of solids 122 or sand grains. Where the measured pattern of intensity values matches the known intensity value pattern or set of patterns, the processing circuitry 130 may determine from the amplitude and duration of the matched pattern that solids 122 or sand grains are present. In addition, matching the measured pattern of intensity values to a known intensity value pattern can yield information about the solids 122 or sand grains themselves. For example, there may be different known intensity value patterns for different types or sizes of solids 122 or sand grains, or for different fractional percentages of the solids 122 or sand grains in the multiphase fluid. Thus, by matching the measured pattern of intensity values to a known intensity value pattern, in addition to determining that solids 122 or sand grains are present, a type of solids 122 or sand grains, size of the solids 122 or sand grains, number of the solids 122 or sand grains, or fractional percentage of the solids 122 or sand grains in the multiphase fluid may be determined. The known intensity value patterns may be a priori knowledge gathered experimentally, through modeling, or from a database.

Rather than analyzing the measured pattern of intensity values in the time domain, the processing circuitry 130 may instead analyze the pattern of intensity values in the frequency domain. Therefore, the processing circuitry 130 may perform a Fourier transform on the measured pattern of intensity values to yield a pattern or spectrum of measured frequencies. A filtering may then optionally be applied by the processing circuitry 130 to the spectrum of measured frequencies to as to reject certain frequencies, and the result (or the original spectrum, in the case where filtering is not performed) compared to a known frequency pattern or set of patterns. Where the spectrum of measured frequencies matches the known frequency pattern or set of patterns, the processing circuitry 130 determines that solids 122 or sand grains are present.

Matching the spectrum of measured frequencies to a known frequency pattern can yield information about the solids 122 or sand grains themselves. For example, there may be different known frequency patterns for different types or sizes of solids 122 or sand grains, or for different fractional percentages of the solids 122 or sand grains in the multiphase fluid. Thus, by matching the spectrum of measured frequencies to a known frequency pattern, in addition to determining that the solids 122 or sand grains are present, a type of the solids 122 or sand grains, size of the solids 122 or sand grains, number of solids 122 or sand grains, or fractional percentage of the solids 122 or sand grains in the multiphase fluid may be determined. The known frequency patterns may be a priori knowledge gathered experimentally, through modeling, or from a database.

Stated another way, the analysis performed by the processing circuitry 130 may be used to identify presence of a frequency band in the spectrum of measured frequencies that indicates the presence of solids 122 such as sand. From this, the phase fraction of solids 122 or sand may be determined. In making this determination, data from an empirical model (itself based on experiment and simulation) may be combined with the determined sizes and numbers of solids 122 present.

In some applications, the processing circuitry 130 may perform analysis on the pattern of measured intensity values in both the time domain and frequency domain, and correlate the results to one another so as to improve accuracy of the pattern matching.

As explained above, this measured intensity over time yields a pattern of intensity values, where some intensity values are greater than others. Thus, stated another way, the pattern of intensity values includes drops in intensity. As explained, where a solid 122, such as a grain of sand, passes through the collimated light, the photodetector 116 registers a drop in intensity for a short period of time. The drop in intensity may be a substantial decrease in intensity, and may be greater than 5%, 15%, or 20% for example. The drop in intensity may also or instead be a drop in intensity during a window of interest, as will be explained below. Through the analysis described above, the duration of this intensity drop can be correlated to the size of the solid 122, while the number of intensity drops can be correlated to the number of solids 122 or sand grains present.

In correlating the duration of the drop in intensity to the size of the solids 122 or sand grains, the diameters of the solids 122 or sand grains is estimated as a function of the duration of the intensity drop. From the diameters of the solids 122 or sand grains, the processing circuitry 130 can, where desired, calculate a total volume of solids 122 or sand grains.

In the case where the processing circuitry 130 continuously adjusts the power of the lasers 106a-106c dependent upon the output level of the photodetectors 116, the processing circuitry 130 accordingly increases the power of the lasers 106a-106c, such that the power of the lasers 106a-106c increases suddenly in correspondence to the intensity drop registered by the photodetector 116. Thus, in this application, the processing circuitry 130 measures and analyzes the power output of the lasers 106a-106c over time, and the operations and analysis described above can be performed on the pattern of measured power outputs of the lasers 106a-106c.

Thus, the duration of this power increase or decrease of the lasers 106a-106c can be correlated to the size of the solids 122 or sand grains, while the number of power increases or decreases of the lasers 106a-106c can be correlated to the number of solids 122 or sand grains present. In correlating the duration of the power increase of the lasers 106a-106c to the size of the solids 122 or sand grains, the diameters of the solids 122 or sand grains is estimated as a function of the duration of the power increase of the lasers 106a-106c. From the diameters of the solids 122 or sand grains, the processing circuitry 130 can, where desired, calculate a total volume of solids 122 or sand grains.

The monitoring and measurement of the output of the photodetector 116, as described above, may be performed by the processing circuitry 130. Optionally, the photodetector 116 may use an estimate of the instantaneous velocity of the solids 122 or sand grains (determined separately from cross-correlation velocimetry and/or laser Doppler measurement) to determine a window of interest in which the intensity drops, or measured patterns (in either time domain or frequency domain) are to occur if they are to indicate presence of the solids 122 or sand grains.

The specific use of the light 113 reflected or scattered from solids 122 or sand grains in the multiphase fluid, as detected by photodetector 120, will now be discussed. In addition to solids 122, bubbles or droplets 124 may also result in an intensity drop, or change in the measured pattern of intensity values, as they pass through the collimated light. To distinguish between solids 122 or sand grains, and bubbles or droplets 124, the photodetector 120 is used to detect light 113 scattered from solids 122 or sand grains, and/or bubbles or droplets 124, as the scattering behavior of solids 122 such as sand grains is different than that of bubbles or droplets 124. The processing circuitry 130 performs spectral analysis to distinguish whether the scattered light 113 was scattered from the solids 122 or sand grains, or the bubbles and droplets 124, and the results of this spectral analysis may be taken into account when performing the time domain and frequency domain pattern matching described above so as to provide for a more accurate determination of the solid phase fraction of the multiphase fluid by the processing circuitry 130, and for a more accurate determination of the gas phase fraction of the multiphase fluid by the processing circuitry 130, since light 113 scattering from bubbles 124 indicates the presence of bubbles of gas.

Yet another way to determine the phase fraction of the solids 122 or sand grains is through the use of a machine learning setup, such as a neutral network employing a reinforcement learning algorithm. The neutral network is set up by being fed known training data, and from that, learns how to determine the phase fractions of the solids 122 or sand grains by monitoring the output of the photodetectors 116 and 120.

Figure 4:
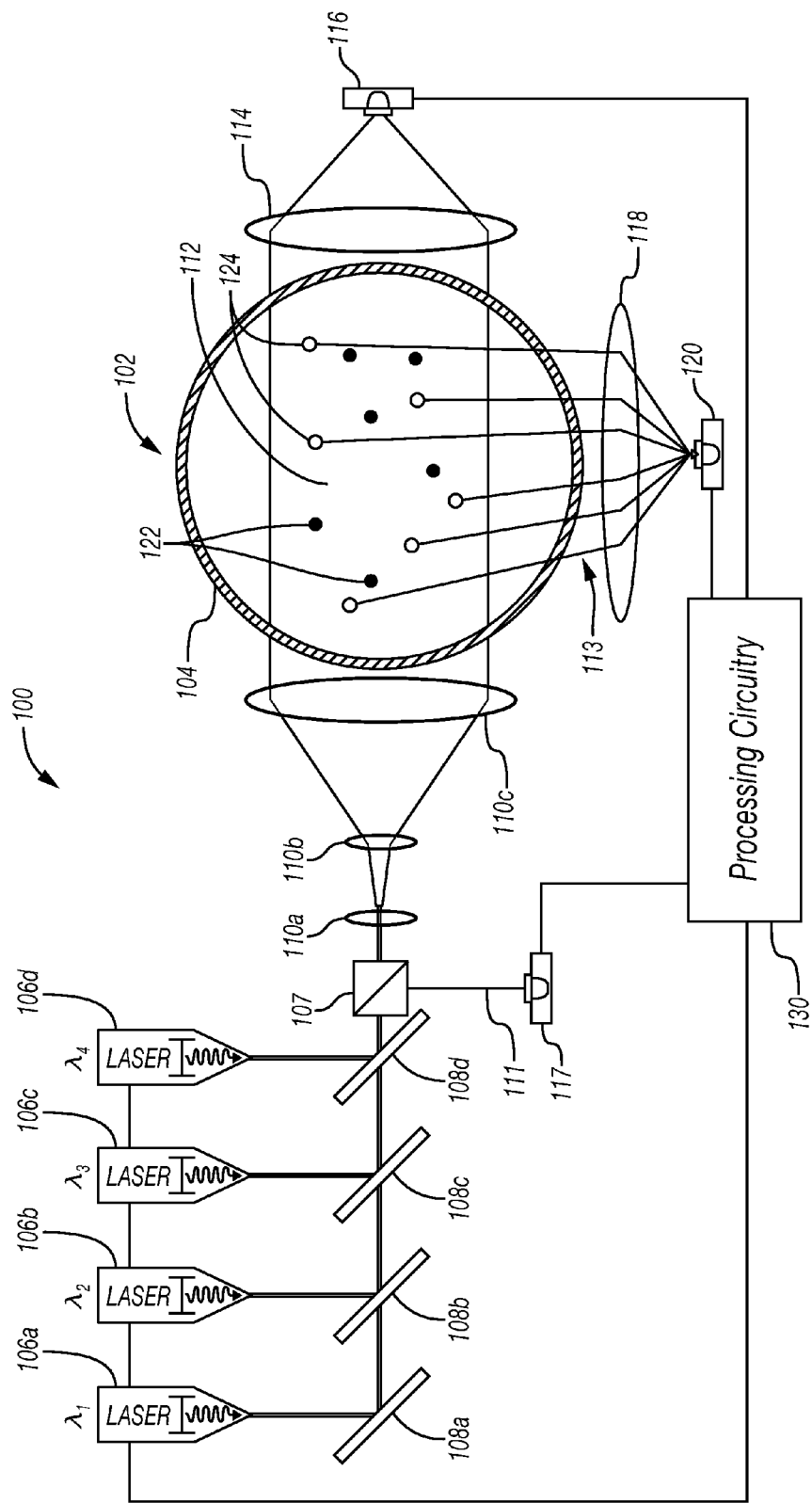
FIG. 4 is a schematic block diagram of a phase fraction determination system similar to that of FIG. 2 but with an additional collimated laser source to assist with discrimination among four phases.

A fourth laser 106d and its corresponding dichroic mirror 108d may also be used in sand detection, as shown in the embodiment of FIG. 4. Here, the fourth laser 106d also emits laser light along the optical path through the window 104 and into the multiphase fluid. The wavelength $\lambda_4$ of the fourth laser 106d is chosen to be close to, or at, an absorption peak of the phase of interest, such as, for example, sand species of interest, hydrogen sulfide, or any other desired phase, but at which wavelength $\lambda_4$ the optical density of the multiphase fluid does not exceed an amount that would render the emitted laser light undetectable under attenuation. The data on detected attenuation due to sand absorption, or absorption of any other phase of interest, can be used by the processing circuit 130 to enhance the outputs of the sand, or solid 122, phase fraction determination as described above, using the techniques described.

Any number of additional lasers may be used, with each laser emitting at a wavelength chosen to be close to, or at, an absorption peak of a phase of interest. Thus, it is to be understood that the system disclosed herein is capable of determining the phase fraction of any number of phases of a multiphase fluid.

Figure 3:
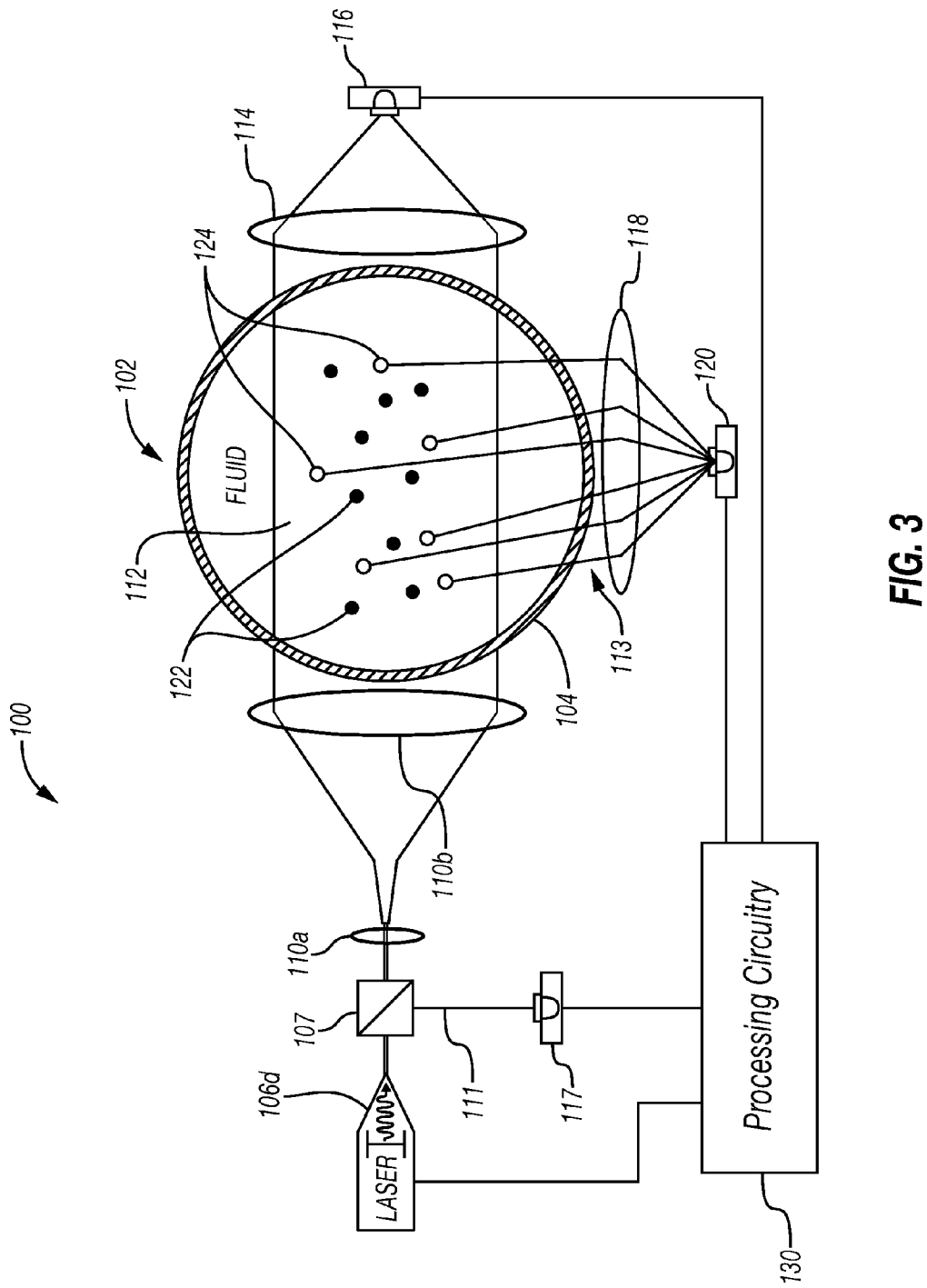
FIG. 3 is a schematic block diagram of a phase fraction determination system capable of sand detection, in accordance with this disclosure.

Since sand can be particularly damaging to production systems, in some applications it may be desirable to make a solid detector for determining a phase fraction of solids 122 within a multiphase flow, but without determining the phase fractions of gas, oil, and water. To that end, one embodiment shown in FIG. 3 may include the third laser 106d, but not the other lasers. Since temporal multiplexing need not be used in this embodiment, the third laser 106d may directly emit light along the optical path toward the window 104, and a mirror need not be present. This embodiment functions to detect solids 122 and to determine the phase fractions of solids 122 in the multiphase fluid from the scattered light 113 as described above with reference to FIG. 3.

In the specification and appended claims: the terms "connect," "connection," "connected," "in connection with," and "connecting" are used to mean "in direct connection with" or "in connection with via one or more elements;" and the term "set" is used to mean "one element" or "more than one element." Further, the terms "couple," "coupling," "coupled," "coupled together," and "coupled with" are used to mean "directly coupled together" or "coupled together via one or more elements." As used herein, the terms "up" and "down," "upper" and "lower," "upwardly" and "downwardly," "upstream" and "downstream;" "above" and "below;" and other like terms indicating relative positions above or below a given point or element are used in this description to more clearly describe some embodiments of the disclosure.

Although the preceding description has been described herein with reference to particular means, materials and embodiments, it is not intended to be limited to the particulars disclosed herein; rather, it extends to all functionally equivalent structures, methods, and uses, such as are within the scope of the appended claims. Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

The invention claimed is:

1. An apparatus comprising:
    a structure containing a multiphase fluid;
    a transparent window structure formed in the structure;
    a collimated light source configured to emit light through the transparent window structure and into the structure, the emitted light having a wavelength at which a component of a desired phase of the multiphase fluid is absorptive;
    a photodetector positioned such that the emitted light passes through the multiphase fluid in the structure and out through the transparent window structure to impinge upon the photodetector;
    wherein the photodetector has an actual dynamic range for collimated light detection; and processing circuitry coupled to the collimated light source and the photodetector, the processing circuitry configured to:
adjust a power of the collimated light source in a series of steps dependent upon a relationship between an output level of the photodetector and at least one threshold so as to cause measurement of the emitted light by the photodetector over an effective dynamic range greater than the actual dynamic range; and
determine at least one property of the multiphase fluid as a function of the measured emitted light.

2. The apparatus of claim 1, wherein the processing circuitry adjusts the power of the collimated light source in the series of steps dependent upon the relationship between the output level of the photodetector and the at least one threshold by:
switching the power of the collimated light source from a higher step to a lower step when the output level of the photodetector exceeds an upper threshold; and
switching the power of the collimated light source from the lower step to the higher step when the output level of the photodetector falls below a lower threshold.

3. The apparatus of claim 1, wherein the emitted light passes through substantially an entire cross sectional area of the multiphase fluid in the structure.

4. The apparatus of claim 1, further comprising at least one lens associated with the collimated light source for shaping the emitted light into a ribbon shape.

5. The apparatus of claim 1, wherein the collimated light source comprises a first collimated light source having a first wavelength at which a component of a first phase of the multiphase fluid is absorptive; and further comprising a second collimated light source having a second wavelength at which a component of a second phase of the multiphase fluid is absorptive, and a third collimated light source having a third wavelength at which components of the first and second phases of the multiphase fluid are not absorptive.

6. The apparatus of claim 5, wherein the first phase of the multiphase fluid comprises oil; wherein the second phase of the multiphase fluid comprises water; wherein a third phase of the multiphase fluid comprises gas; and wherein the at least one property of the multiphase fluid comprises phase fractions of gas, oil, and water.

7. The apparatus of claim 5, wherein the first wavelength is substantially at a hydrocarbon peak absorption band; wherein the second wavelength is at a water absorption band where water is more absorptive of light than oil; and wherein the third wavelength is at a band where neither water nor oil is substantially absorptive.

8. The apparatus of claim 5, wherein the processing circuitry is configured to differentiate between sand, and bubbles or droplets.

9. The apparatus of claim 5, wherein the processing circuitry is configured to pulse the first, second, and third collimated light sources in a pattern such that but one of the first, second, and third collimated light sources is emitting light at a time.

10. The apparatus of claim 5, wherein a fourth phase of the multiphase fluid comprises a solid phase; further comprising a fourth collimated light source having a fourth wavelength at which components of the solid phases of the multiphase fluid are absorptive.

11. The apparatus of claim 5, wherein the processing circuitry is configured to pulse the first, second, and third collimated light sources simultaneously and at different pulsing frequencies from one another, and is configured to perform phase-sensitive detection simultaneously for the first, second, and third collimated light sources.

12. The apparatus of claim 11, wherein the processing circuitry is configured to discriminate between components of the emitted light impinging upon the photodetector that were emitted by the first collimated light source, components of the emitted light impinging upon the photodetector that were emitted by the second collimated light source, and components of the emitted light impinging upon the photodetector that were emitted by the third collimated light source, using the phase-sensitive detection.

13. The apparatus of claim 5, wherein:
the first collimated light source comprises a first laser light source configured to emit laser light along a path that does not include the transparent window structure, and a first mirror configured to reflect the laser light from the first laser light source along a path that includes the transparent window structure;
the second collimated light source comprises a second laser light source configured to emit laser light along a path that does not include the transparent window structure, and a second mirror configured to reflect the laser light from the second laser light source along a path that includes the transparent window structure; and
the third collimated light source comprises a third laser light source configured to emit laser light along a path that does not include the transparent window structure, and a third mirror configured to reflect the laser light from the third laser light source along a path that includes the transparent window structure;
and further comprising:
at least one lens to focus the reflected laser light from the first, second, and third laser light sources.

14. The apparatus of claim 1, further comprising an additional photodetector positioned such that emitted light that scatters off the multiphase fluid and out through the transparent window structure impinges upon the additional photodetector; wherein the processing circuit is configured to measure the scattered emitted light; wherein the processing circuitry also determines the at least one property of the multiphase fluid as a function of the measured scattered emitted light; and wherein the at least one property comprises a phase fraction of solids in the multiphase fluid.

15. A method of determining at least one property of a multiphase fluid comprising:
emitting collimated light from a collimated light source into the multiphase fluid, the emitted collimated light having a wavelength at which a component of a desired phase of the multiphase fluid is absorptive;
measuring the emitted collimated light by detecting light passing through the multiphase fluid impinging upon a photodetector having an actual dynamic range for collimated light detection;
adjusting a power of the collimated light source in a series of steps dependent upon a relationship between an output level of the photodetector and at least one threshold so as to cause measurement of the emitted collimated light by the photodetector over an effective dynamic range greater than the actual dynamic range; and
determining at least one property of the multiphase fluid as a function of the measured emitted collimated light.

16. The method of claim 15, wherein adjusting the power of the collimated light source in the series of steps dependent upon the relationship between the output level of the photodetector and the at least one threshold comprises:

switching the power of the collimated light source from a higher step to a lower step where the output level of the photodetector exceeds an upper threshold; and switching the power of the collimated light source from the lower step to the higher step where the output level of the photodetector falls below a lower threshold.

17. The method of claim 15, wherein measurement of the emitted collimated light by the photodetector over time yields a pattern of intensity values; and wherein determining the at least one property of the multiphase fluid as a function of the measured emitted collimated light comprises determining presence of sand grains as a function of the pattern of intensity values.

18. The method of claim 17, wherein the presence of the sand grains is determined as a function of the pattern of intensity values by performing a Fourier transform on the pattern of intensity values, and determining the presence of the sand grains by matching a frequency pattern output by the Fourier transform to a known sand grain frequency pattern.

19. The method of claim 17, wherein the presence of the sand grains is determined as a function of the pattern of intensity values by correlating the pattern of intensity values to a known sand grain intensity value pattern.

20. The method of claim 17, further comprising determining at least one of sizes of the sand grains and a number of the sand grains as a function of the pattern of intensity values.

* * * * *